United States Patent [19]

Abrams

[11] Patent Number: 4,613,325

[45] Date of Patent: Sep. 23, 1986

[54] FLOW RATE SENSING DEVICE

[76] Inventor: Lawrence M. Abrams, 32 Herrick Dr., Lawrence, N.Y. 11559

[21] Appl. No.: 564,332

[22] Filed: Dec. 22, 1983

Related U.S. Application Data

[63] Continuation-in-part of Ser. No. 399,825, Jul. 19, 1982, abandoned.

[51] Int. Cl.$^4$ .......................... A61M 5/14; G01F 1/38
[52] U.S. Cl. ...................................... 604/65; 604/118; 604/246; 128/DIG. 13; 73/861.47; 73/861.52
[58] Field of Search ...................... 604/51–53, 604/65–67, 93, 118, 245–246, 31, 149; 128/DIG. 13; 73/861, 861.42, 861.47, 861.52

[56] References Cited

U.S. PATENT DOCUMENTS

| | | | |
|---|---|---|---|
| 2,365,573 | 12/1944 | McGay | 73/861.52 |
| 3,930,742 | 1/1976 | Boyce | 73/861 |
| 4,043,332 | 8/1977 | Metcalf | 604/141 |
| 4,216,673 | 8/1980 | November | 73/861 |
| 4,240,294 | 12/1980 | Grände | 73/861.47 |
| 4,277,227 | 7/1981 | Jenkins | 604/245 |
| 4,299,220 | 11/1981 | Dorman | 604/118 |
| 4,340,050 | 7/1982 | Noiles | 604/246 |

FOREIGN PATENT DOCUMENTS

WO81/00519  3/1981  PCT Int'l Appl. .................. 604/31

Primary Examiner—C. Fred Rosenbaum
Assistant Examiner—Michelle N. Lester
Attorney, Agent, or Firm—Hammond & Littell, Weissenberger & Dippert

[57] ABSTRACT

A flow rate sensing device, particularly for use in regulating the rate of flow in a system for parenteral administration of liquids to patients. The liquid emerges from a storage reservoir and is fed into a housing through an upstream flow passage portion and then is made to pass through a narrow throat passage wherein the velocity of the liquid increases while its pressure decreases. The liquid then emerges into a downstream flow through passage and flows through an outlet from the housing. In an intravenous fluid administration system, the housing outlet is connected to a terminal tubing section and an intravenous needle. A pressure transducer, consisting of two chambers separated by a resilient deformable diaphragm, has its upstream chamber in fluid and pressure communication with the upstream flow path portion and its downstream chamber in fluid and pressure communication with the flow emerging from the throat passage. Variations in the flow rate through the throat passage effect changes in the pressure differential between the transducer chambers and thus cause variable degrees of displacement of the transducer diaphragm. The mechanical signals created by the movement of the diaphragm can be transduced to an arrangement for controlling the rate of fluid flow through the system. Alternatively, the mechanical signal created by the diaphragm can be transduced to flow rate monitoring or flow rate coordinating systems.

21 Claims, 3 Drawing Figures

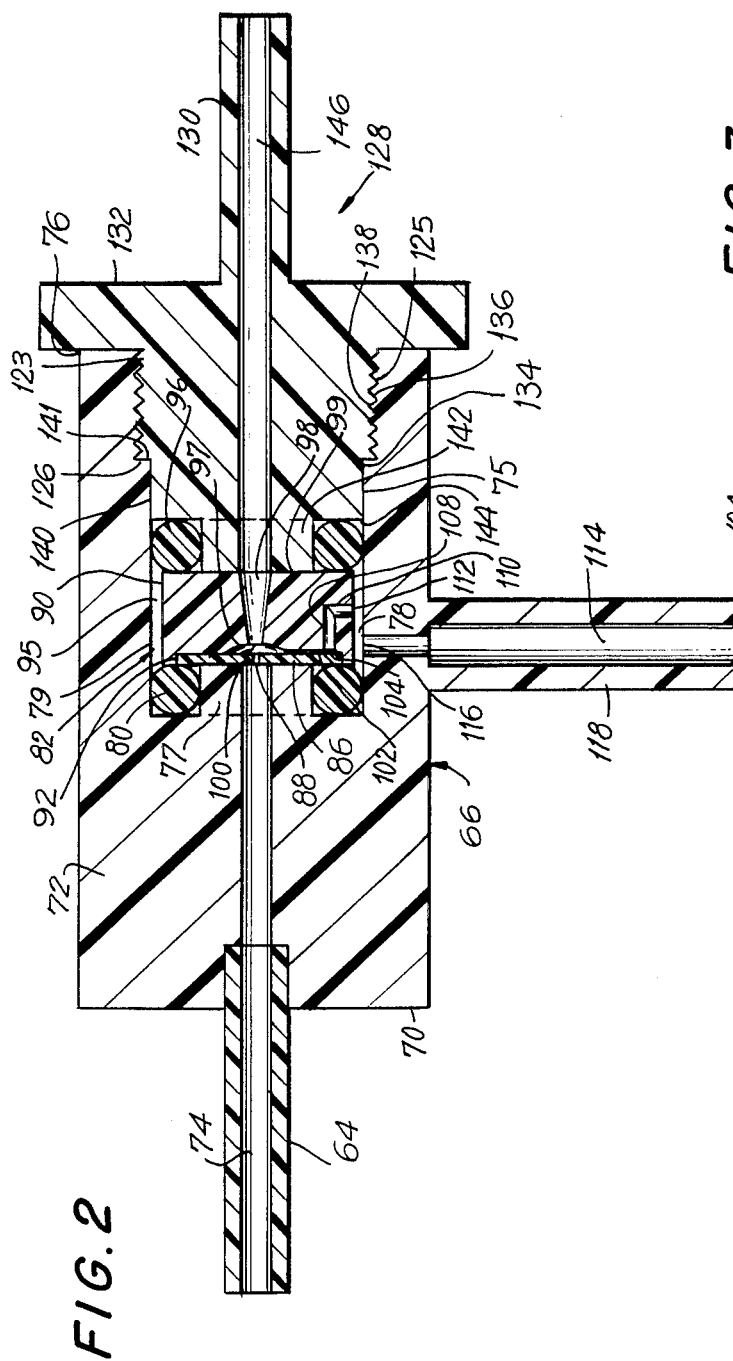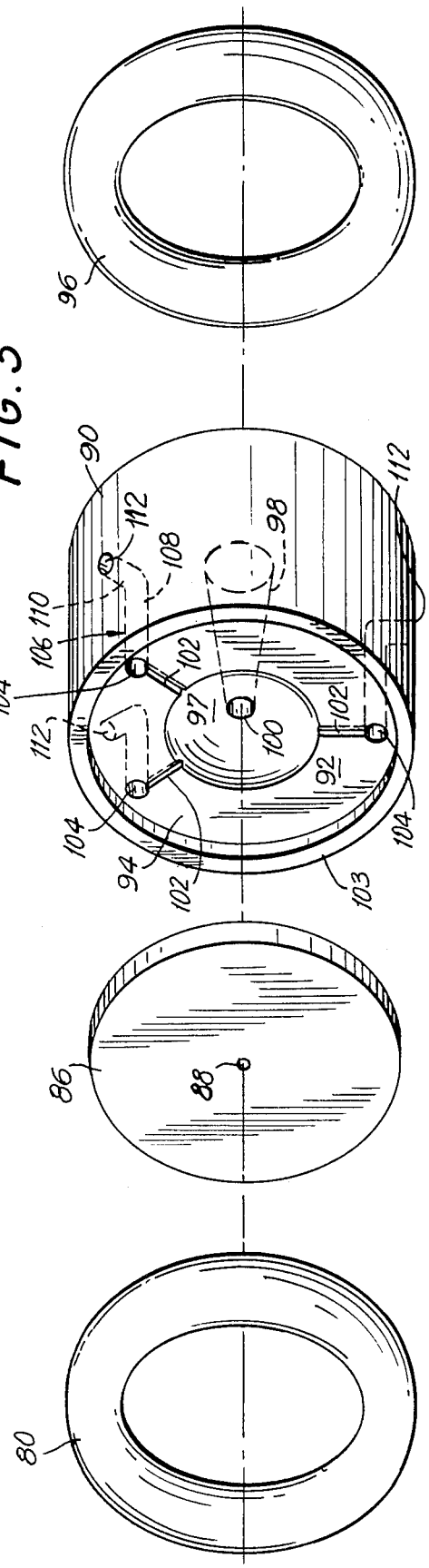

4,613,325

FLOW RATE SENSING DEVICE

BACKGROUND OF THE INVENTION

This application is a continuation-in-part of application Ser. No. 06/399,825, filed July 19, 1982 abandoned.

1. Field of the Invention

The present invention relates generally to flow rate sensing devices, and particularly to such devices utilized to regulate the rate of flow of liquids to be administered to a patient.

2. Description of the Prior Art

A variety of systems have been utilized to supply or administer various liquids, including, by way of example, blood, nutrient solutions, pharmaceutical solutions, and so on to human and animal patients. For instance, when intravenous administration of liquids is desired, the most commonly used apparatus to achieve such administration comprises a container for the liquid to be administered, a tube connected to the container, and a hollow needle at the end of the tube to be introduced into the patient's vein, with the fluid flowing under gravity out of the container through the tube. Frequently, some manually operated mechanical device is provided, such as an adjustable clamp, for controlling the rate of flow from the storage container into the patient. Obviously, this clamp does nothing more than vary the resistance in the tube to the fluid flow, and the actual flow rate is dependent in addition on the pressure of the fluid passing through the tube, which is in turn a function of the differential in height between the level of liquid in the container and the point of administration to the patient.

In the above described commonly used gravity systems, the rate of flow into the patient, i.e., the quantity of liquid administered to the patient per unit time, is subject to substantial fluctuation. The main causes for these fluctuations in flow rate are changes in the mechanical resistance in the tube near the adjustable clamp (caused, for example, by slippage of the clamp) and in the hollow needle inserted into the patient, resistance to outflow near the end of the needle, the height differential between the liquid level in the container and the point of administration to the patient, and the back pressure exerted against the fluid flow, for example, by the patient's venous blood pressure. In addition, different fluids will encounter different degrees of resistance when flowing through the same system as a result of differences in density, viscosity and flow properties, and hence will flow at different rates. As a result of the aforementioned and other factors, even though a transparent drip chamber is frequently provided in these gravity systems whereby the rate of drops flowing from the container into the tube can be observed and measured per unit time, the actual rate of fluid outflow from the administering system and into the patient is quite variable. Moreover, the volume of the drops is neither constant nor precise, and their number is not a true indication of flow rate.

The problems caused by the fluctuations in flow rate experienced with the widely used gravity systems can be serious. In the case of certain medicinal liquids which must be administered to a patient, it is highly desirable to maintain a constant rate of flow into the patient to keep the blood or tissue levels of the medicinal substances in the administered liquid at or near predetermined values. In addition, in the case of transfusions, such as of blood, it is frequently extremely important to maintain a steady flow of the transfused fluid into the patient to keep the patient's blood pressure at a fairly constant level.

Improved systems for the administration of liquids to patients have been proposed in the prior art to overcome some of the drawbacks of the gravity-based systems. These improved systems are essentially of two types. In the first type, an attempt is made to provide means for controlling the resistance to flow through the system in a more accurate and refined manner than the standard adjustable clamp which constricts the tube through which the fluid flows. For example, mechanical variable resistant devices have been interposed in the fluid flow line which do not require constriction or crimping of the tubing but instead provide flow-through apertures of various sizes, depending on the degree of resistance desired. These variable resistance devices obviously do not control flow rate directly but are premised on the assumption that the pressure head of the fluid passing through the variable resistance is constant and, thus, for each resistance setting a particular constant flow rate will result. In fact, however, as indicated previously, because of variations in the height differential between the liquid in the container and the point of administration to the patient, as well as variations in the resistance in the needle and in the back pressure from the patient, merely maintaining a fixed degree of resistance at a point in the flow line downstream of the container and upstream of the needle does not insure a constant rate of flow into the patient.

A second group of improved prior art devices attempts to regulate by a variety of means the pressure head of the fluid flowing from the container or bag. For example, it has been proposed to pressurize the liquid in a deformable container or bag by using an external or an internal gas-filled bladder which transmits the pressure therein to the liquid in the bag, ostensibly to maintain a constant pressure on the liquid and therefore a constant flow rate at the point of administration. However, this technique does not maintain constant pressure on the liquid in the bag because the expansion in the bladder causes a drop in the pressure of the gas therein, and changes in the ambient temperature cause pressure fluctuations in the bladder as well which would result in pressure fluctuations in the liquid exiting the bag. Other proposals have been made to pressurize a liquid in a container bag by use of weights, rollers and springs, but in each instance there is variation in flow rate as the liquid is discharged from the bag.

In U.S. Pat. No. 4,043,332, a flow rate liquid medicament administering device is disclosed which allegedly maintains constant flow into the patient by means of pressure control in the fluid flow line. That device incorporates a flow rate regulator which is activated by a pressure differential between its inlet and outlet. The pressure differential is created by directing one portion of the fluid flow through a throttling mechanism to reduce its pressure and thence into one chamber of a container while another portion of the fluid flow bypasses the throttle and enters a second, dead-end chamber of the same container, the two chambers being divided by a flexible, deformable membrane or diaphragm which is in mechanical communication with a valve stem. The pressure of the fluid in the chamber fed by the bypass is normally higher than the pressure of the fluid in the chamber on the opposite side of the diaphragm which is fed from the throttling element. When the fluid pressure differential between the respective chambers exceeds a predetermined level, the diaphragm is deformed away from the high pressure chamber and the valve stem in communication with the diaphragm is urged into a valve seat, restricting the flow exiting the lower pressure chamber. Conversely, when the pressure differential falls below a predetermined level, the diaphragm is deformed in a direction away from the lower pressure chamber. In this manner, the rate of fluid flow reaching the point of administration is purportedly kept constant.

The device disclosed in U.S. Pat. No. 4,043,332 suffers from a number of defects. In the first place, the device is overly complex and has too many distinct structural elements, many of which contain moving parts, requiring a great deal of expense and effort to manufacture and maintain. This complexity and expense is highly undesirable in a device to be used presumably on an extremely wide basis in hospitals and other health care institutions where fluid administratio,n to patients is universally prevalent. Furthermore, it would be extremely difficult to cheaply manufacture the device disclosed in that patent so that it could be made entirely disposable, as are most prior art intravenous administration units. A nondisposable device necessitates extensive cleaning and sterilization procedures between administrations and particularly when the device is to be used on different patients.

Additionally, the device disclosed in U.S. Pat. No. 4,043,332 is admittedly only operative when a relatively high pressure head is generated in the fluid exiting the storage container and entering the flow regulating elements so that a significant differential can be created by the throttling mechanism between the high and low pressure chambers on either side of the diaphragm. To create this high pressure head in the fluid leaving the container, it is proposed to use a gas-filled pressurized bladder which is put in contact with the fluid in a deformable bag, or to use external pumping means. This requirement for creating artificially high pressures to make the flow control features of the device operative is a significant drawback because it requires activation, and probably constant observation, by the operator of not only the fluid flow and all the elements connected therewith but also of the pressurizing means to ensure that adequate high pressure is being maintained on the fluid in the container to keep the device functioning. Furthermore, maintaining the required pressure becomes increasingly difficult as the level of fluid in the bag falls.

Probably the most significant drawback of the pressure-controlling device of U.S. Pat. No. 4,043,332 is that it does not directly sense or control the rate of flow of fluid through the system and into the patient but instead senses and regulates only a pressure differential between the upstream and downstream portions of the flow line. This system does not take into account variations in the total resistance to flow which will decrease or increase the rate of outflow from the system even when the sensed pressure differential is being maintained at a constant pre-determined level. For example, fluids of different viscosities, densities, and/or other flow properties will flow at different rates even though the effective driving pressure exerted on them is the same. Similarly, changes in mechanical resistance in the system may affect the rate of flow but will not be accurately compensated for by a system that can only detect the difference in fluid pressure between two portions of the flow line, which pressure differential is not a function of flow rate.

Until the present, therefore, there has been no device for sensing the rate of flow in a system administering the fluid to a patient which is capable of maintaining a constant rate of flow into the patient without requiring the pressurization of the fluid in the storage bag or container, particularly not a device of this nature which is simple and cheap to manufacture and is composed of a relatively few simple parts, can readily be made disposable, and can be interposed in conventional flow systems such as a conventional gravity-flow resistance line with or without a mechanical variable resistance device.

SUMMARY OF THE INVENTION

1. Objects of the Invention

It is an object of the present invention to provide a novel flow rate sensing device which is capable of maintaining a constant flow rate in fluid administering devices and which is not subject to any of the foregoing disadvantages of the prior art.

It is another object of the invention to provide a device of the character described which will enable the supply of liquids to a patient at a substantially constant flow rate which essentially is independent of the head pressure, the back pressure, and the inherent density, viscosity or flow properties of the liquid being administered.

Yet another object of the invention is to provide a device of the character described which is operative for maintaining a substantially constant flow rate without requiring external pressurization of the fluid storage container.

A further object of the invention is to provide a device of the character described which is capable of maintaining a substantially constant flow rate within a wide variation of height differentials between the fluid in the container and the point of administration.

Yet a further object of the invention is to provide a flow rate sensing device which can be incorporated into systems for monitoring flow rate or coordinating flow rate with a second fluid administration system.

Still another object of the invention is to provide a device of the character described which comprises relatively few and simple parts, is inexpensive and easy to manufacture, and can readily be made disposable so that a new, sterile device can be utilized for each patient.

Yet a further object of the invention is to provide a device of the character described which is compatible with prior art liquid administration systems that are gravity operated and may optionally incorporate a mechanical variable resistance device.

Still an additional object of the present invention is to provide a flow rate regulator that can be used in parallel with prior art regulators.

Yet another object of the invention is to provide a device of the character described which is portable, nonelectric and light in weight.

These and other objects and advantages of the present invention will become evident from the description that follows.

2. Brief Description of the Invention

In keeping with these objects and others which will become apparent hereinafter, the invention resides, briefly stated, in a flow rate sensing device, particularly for use in regulating the rate of flow in a system for parenteral administration of a liquid wherein the head pressure of the liquid emerging from a reservoir, the back pressure resisting fluid flow, the viscosity and density of the liquid selected, and the mechanical resistance to flow through the system may all be variable, which device comprises a housing having a fluid inlet for permitting ingress of a fluid from a flow line and a fluid outlet for permitting egress of the fluid from the housing into another portion of the flow line. An upstream flow path portion is in fluid communication with the housing inlet and a downstream flow-through passage is in fluid communication with the housing outlet.

A flow-through throat passage is situated intermediate and in fluid communication with both the upstream flow path portion and the downstream flow-through flow path portion, defining a fluid flow path from the fluid inlet of the housing outlet through the upstream passage, the throat passage, the downstream passage and the housing outlet, successively. The throat passage is substantially narrower, i.e., has a substantially smaller median flow-through cross-sectional area than either the upstream path portion or the downstream passage. Thus, in accordance with Bernoulli's Law, the fluid flowing through the throat with its reduced flow-through cross-sectional area will flow at a higher velocity and at reduced pressure in comparison with the fluid flowing in the upstream path portion. In the device of the present invention, a means is provided for detecting the differential between the pressure of the fluid flowing in or just downstream of the throat passage and the pressure of the fluid in the upstream path portion, which pressure differential varies with the velocity of the fluid.

The pressure differential between the fluid in the throat passage and the fluid in the upstream path portion is sensed by a pressure transducer capable of putting out a signal which varies in intensity in accordance with the magnitude of the detected pressure differential. If regulation of flow rate is desired, as in the preferred embodiments of the invention, the pressure transducer puts out an electrical or mechanical signal operative for controlling a valve or other flow restriction means.

Thus, for example, if the flow rate through the throat passage exceeds a predetermined level, increasing the differential between the fluid flowing through the throat passage and the fluid in the upstream path portion, said pressure values measured generally normal to the direction of fluid flow, the pressure transducer will signal the valve or other flow restriction means to reduce the rate of flow through the line. Conversely, if the velocity of the fluid through the throat passage falls below the predetermined level and the pressure differential being detected thus decreases, the transducer will signal the valve or other flow restriction means to permit a higher rate of flow through the line.

The flow-rate sensing device of the present invention is not restricted to use as a flow rate regulator. Instead of outputting a signal to a flow restriction means or a valve to reduce the flow rate when an excessive lateral or normal pressure differential is detected between the fluid in the throat passage and the fluid in another passage portion, the transducer can output a variety of other signals. For example, the transducer can be linked to an electronic visual display system to provide a visual readout, whether digital, graphic or otherwise, indicating the flow rate at any particular point in time. In another application of the device of the present invention, the transducer can be linked to an alarm system to alert hospital or other health care personnel to a potentially dangerous reduction or increase in the rate of flow of the fluid being administered to the patient. Still further, the transducer could be linked to a second flow line carrying another liquid being administered to the patient to regulate the rate of flow of that second liquid in accordance with variations in the rate of flow of the first liquid.

Various other applications and uses for the flow sensing device of the present invention, particularly in the fields of medicine and surgery, will be readily apparent to those skilled in the art upon reading the detailed description of the invention set forth herein. The novel features which are considered as characteristic of the invention are set forth in particular in the appended claims. The invention itself, however, both as to its construction and its methods of operation, together with additional objects and advantages thereof, will be best understood when the description of the preferred embodiments is read in connection with the accompanying drawings.

BRIEF DESCRIPTION OF THE DRAWINGS

FIG. 2 is an enlarged sectional view taken substantially along line 2—2 of FIG. 1 and showing the principal component of a flow rate sensing device in accordance with the present invention.

FIG. 3 is an exploded view of some of the internal members of the component shown in FIG. 2.

DESCRIPTION OF THE PREFERRED EMBODIMENTS

Figure 1:
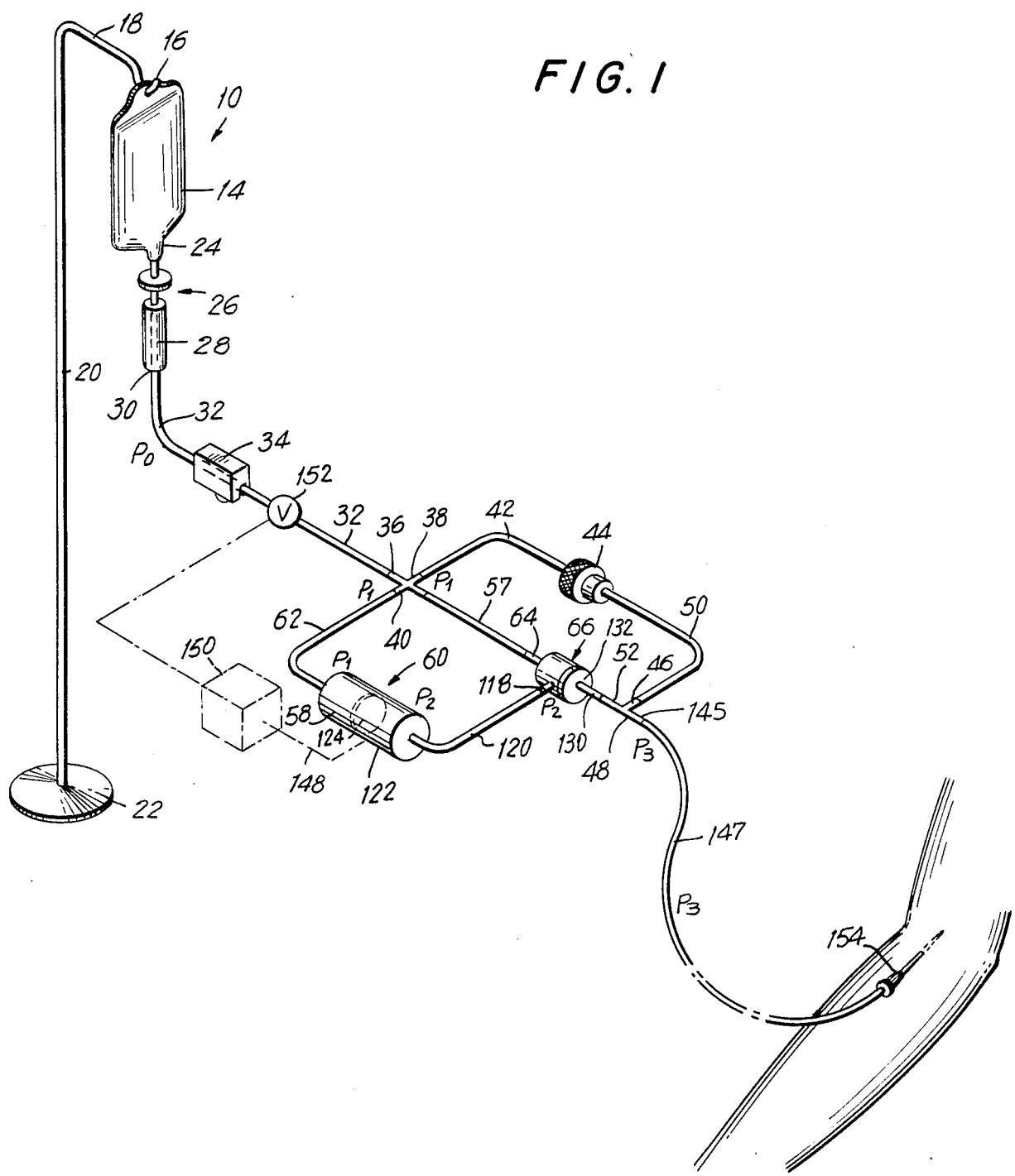
FIG. 1 is a perspective, partially diagrammatic view of a typical system for intravenously adminstering fluids to a patient, incorporating the flow rate sensing device of the present invention.

With reference to to the drawings, FIG. 1 thereof illustrates a typical system, denoted generally as 10, for intravenous administration of liquid to a patient, which system incorporates the flow rate sensing device of the present invention, denoted generally as 12. The liquid to be administered is initially contained within a storage reservoir, shown in FIG. 1 as a storage bag 14 made of a limp, flexible material such as a flexible synthetic plastic. In a gravity flow system, the storage bag is conventionally suspended on a hook 16 which forms the terminus of an arm 18 that extends transversely from a pole or stand 20 supported on the floor by a base 22. Although the arm 18 is shown in FIG. 1 as being fixedly mounted on the pole 20, the arm 18 is often slideably mounted for vertical movement along the pole 20 to vary the height of the storage bag 14 depending on the height of the point of administration to the patient and on the orientation and position of the patient during the administration, e.g., whether the patient will be ambulatory, sitting, lying in bed, and so on.

The storage bag 14 has a downwardly facing mouth 24 at its end which is remote from the hook 16 to which a drip chamber assembly 26 is connected to permit flow from the storage bag into a transparent drip chamber 28. The drip chamber 28 has a fluid outlet at its bottom end 30 to permit the egress of the fluid accumulating therein into an outflow tubing section 32. The drip chamber enables the system operator to observe and ensure that fluid is actually flowing out of the storage bag into the flow line.

The outflow tubing section 32 passes through a manually operable adjustable clamp 34, which enables manual shutting off of the flow from the container 14 if termination of the flow should become necessary. In a system incorporating the flow rate sensing device of the present invention, the adjustable clamp 34 functions as an on-off control and does not act as a flow rate regulator.

Tubing section 32 is detachably connected at its terminus to a four-way tubing joint 36 which has spaced arms 38 and 40 oriented at oblique angles, e.g., at right angles, to the tubing section 32. The arm 38 is frictionally connected to a bypass tubing section 42 which leads to a variable resistance device 44. The variable resistance device 44 can be, for example, any conventional device for creating variable degrees of mechanical resistance in a fluid flow path. An example of such a device is the Dial-A-Flo device marketed by the Sorenson Research Co., Inc.

The variable resistance device 44 is in fluid communication with one arm 46 of a downstream Y-shaped tubing joint 48 via a return tubing section 50. The joint 48 has a second arm 52 spaced apart from the arm 46, and said second arm 52 is connected in turn to a fluid path continuation of the outflow tubing section 32, as will be detailed further below. Thus, the variable resistance device 44 is in a bypass flow path which includes the bypass tubing section 42, the return tubing section 50 and the downstream tubing joint 48.

The second spread arm 40 of the tubing joint 36 is in fluid communication with the upstream chamber 58 of a pressure transducer 60 via a tubing conduit 62. The structure and function of the pressure transducer 60 will be described in detail below.

The tubing joint 36 also joins the outflow tubing section 32 to one end of a connecting tubing section 57, which is in turn joined for fluid communication at its opposite end with a protruding stem 64 of a flow restriction member 66. The flow restriction member 66 is shown in enlarged cross-section in FIG. 2, and some of its internal components are shown in exploded perspective view in FIG. 3.

The structure of the flow restriction member 66 is best seen in the enlarged sectional view of FIG. 2. The stem 64, which is attached to the connecting tubing section 57, is integral and of one piece with the barrel-shaped housing 70 of the flow restriction member 66. The portion of the housing 70 which is adjacent to the stem 64 shall be referred to as the ingress section 72 of the housing 70.

An upstream flow-through passage 74 in the form of an elongated rectilinear bore runs axially through the protruding stem 64 and thence through the ingress section 72 of the housing 70. The flow-through passage 74 is in fluid communication with the connecting tubing section 57, and thus the stem 64 with the upstream flow-through passage 74 provides a fluid inlet means permitting fluid flow into the ingress section 72 of the housing 70. The diameter of the flow-through passage 74 is approximately equal to the interior diameters of the connecting tubing section 57 and the upstream tubing joint 36.

The housing 70 has a substantially hollowed out section 75 beginning approximately at the axial center of the housing and continuing to the downstream end 76 of the housing. A squat cylindrical extension 77 of the ingress section 72 protrudes into the hollow 75 at the upstream end 78 thereof. The flow-through passage 74 runs axially through the approximate center of the extension 77. A resilient O-ring 80 or similar sealing element is seated in the annular recess formed between the extension 77 and the surrounding walls 79 of the hollow 75.

A flow rate-responsive pressure reducing arrangement 82 is positioned downstream of the upstream O-ring 80 and the extension 77, firmly abutting against both of the latter, at the upstream end 78 of the hollow 75. This pressure reducing arrangement, which forms the heart of the flow restriction member 66, comprises two principal elements which may be seen in cross-section in FIG. 2 and in enlarged perspective view in FIG. 3. The first of these elements is a flow passage constricting member, for example, a thin rigid disc 86 preferably fashioned of corrosion-free metal, metal alloy, nylon or rigid synthetic plastic material, with an opening for permitting fluid transit therethrough, such as a rectilinear bore 88 through the approximate center thereof. The disc 86 has a diameter greater than that of the extension 77 of the ingress section 72 but slightly less than that of the second element of the pressure reducing arrangement, namely, a cylinder 90, which is preferably formed of corrosion-free metal, metal alloy or rigid synthetic plastic material and has a circular depression 92 in its upstream face 94 which is adapted for snugly receiving the disc 86.

The disc 86 is seated in the depression 92 of the pressure communicating cylinder 90, and the two elements are positioned at the upstream end 78 of the hollow 75 with the disc 86 abutting against the O-ring and the extension 77. The bore 88 in the disc 86 is in fluid communication with the flow-through passage 74. The bore 88 has a diameter which is substantially less than the diameter of the upstream flow path portion, which comprises the flow path elements from the outflow tubing section 32 through the upstream flow-through passage 74. For example, the ratio of the diameter of the upstream flow path portion to that of the bore can be on the order of 1 to 60, in which case the flow-through cross-sectional area of the bore 88 would be on the order of $2.8 \times 10^{-4}$ that of the upstream path portion. Thus, the disc 86 and the bore 88 form a narrow throat passage through which fluid emerging from the flow-through passage 74 must pass, and the O-ring 80 together with the extension 77 firmly abutting against the disc 86 form a watertight seal to ensure that no fluid escapes radially from the interface between those elements and the disc 86.

The pressure communicating cylinder 90 has a diameter slightly less than that of the upstream portion of the hollow 75 in which it is situated, and an annular cavity 95 is thereby defined between the lateral walls of the cylinder 90 and the walls 79 of the hollow 75.

A second O-ring or similar resilient sealing element 96 is positioned in the hollow 75 downstream of the pressure communicating cylinder 90 and firmly abuts against the downstream face 99 of the cylinder 90. Moreover, the O-ring is of such dimension and resilience that it sealingly presses against the surrounding inner walls 79 of the hollow 75 to prevent the escape of fluid axially downstream of the second O-ring 96 within the hollow 75 and thus forms a fluid tight seal for the annular cavity 95 which surrounds the lateral walls of the cylinder 90.

At the approximate center of the depression 92 formed in the upstream face 94 of the pressure communicating cylinder 90 there is a further shallow bowl-shaped recess 97. When the disc 86 is seated in the depression 92, the bowl-shaped recess 97 is positioned immediately downstream of the flow-through throat passage formed by the bore 88 through the disc 86.

A downstream flow-through passage 98 runs axially through the approximate center of the pressure communicating cylinder 90, flaring in the downstream direction from an inlet portal 100 to an outlet 101 in the downstream face 99 of the cylinder 90. The portal 100 is situated substantially in the center of the bowl-shaped recess 97 in the upstream face 94 of the cylinder 90. The bowl-shaped recess 97 has a diameter intermediate that of the depression 92 and the portal 100.

Shallow radial channels 102 are provided at the floor of the depression 92 in the upstream face 94 of the pressure communicating cylinder 90, each of said channels beginning at the periphery of the bowl-shaped recess 97 and terminating in a hole 104 drilled or otherwise fashioned in the floor of the depression 92. Each of the holes 104 comprises the opening of a substantially L-shaped bore 106 which has an axial leg 108 extending approximately one-half way down the axial length of cylinder 90 and a radial leg 110 adjoined and approximately perpendicular to the end of the axial leg 108. The radial leg 110 of each of the bores 106 terminates in an opening 112 in the lateral walls of the cylinder 90. Thus, each of the channels 102 in conjunction with the bores 106 provides a means for fluid and pressure communication between the fluid stream emerging from the throat passage bore 88 and the annular cavity 95 surrounding the cylinder 90.

Obviously, other suitable means for providing fluid and pressure communication between the throat passage and the cavity 95 could be utilized. For example, the channels 102 could run through the rim 103 which surrounds the depression 92 on the upstream face 94 of the pressure-communicating cylinder 90, and terminate in an opening in the lateral walls of the cylinder 90 adjacent the rim 103, thus eliminating the need for the L-shaped bores 106. Alternatively, a portal could be provided in the wall of the bore 88 itself, with a radial pressure communicating passage leading from that portal to the annular cavity 95 by passing through the edge of the disc 86 and thence through the rim 103 around the depression.

A pressure communicating passage 114 extends from an outlet 116 in the walls 79 of the hollow 75 through a lateral stem 118 that is integral and of one piece with the housing 70. As shown in FIG. 1, the lateral stem 118 is adapted to form a frictional connection with a lateral tubing section 120, which is in fluid communication with a dead-end downstream fluid receiving chamber 122 of the pressure transducer 60. The downstream fluid-receiving chamber 122 and the upstream fluid-receiving chamber 58 of the pressure transducer 60 are separated by a resilient membrane or flexible resilient diaphragm 124, formed of any deformable resilient material such as synthetic flexible plastic, and of small enough thickness to be sensitive to even small variations in the pressure differential between the upstream chamber 58 and the downstream chamber 122. Thus, the disc 86 and the pressure communicating cylinder 90, in cooperation with the transducer 60, operate as a flow rate fluctuation detection means.

The flow-rate sensing device of the present invention essentially comprises the flow restriction member 66 in cooperation with the pressure transducer 60.

The hollow 75 formed in the housing 70 of the flow restriction member has a slightly expanded downstream section 123 provided with female threads 125 on the walls thereof. An annular seat 126 is formed at the juncture of the expanded section 123 and the remaining portion of the hollow 75.

A plug 128 comprises a stem 130, a cap 132 and a plug body 134, all of one piece. The plug body 134 is on the side of the cap 132 remote from the stem 130 and includes a portion 136 adjacent to the cap 132 which is provided with male threads 138 on the outer walls thereof as well as an unthreaded section 140 of reduced diameter remote from the cap 132. A shoulder 141 is formed at the juncture of the threaded portion 136 and the reduced diameter section 140. A squat cylindrical extended section 142 of even smaller diameter than the reduced section 140 of the plug body 134 protrudes from the face 144 of the reduced diameter section 140.

The plug 128 is inserted and screwed into the downstream section of the hollow 75 with the threads 136 on the plug body 134 detachably engaging the female threads 125 on the walls of the downstream section 123 of the hollow 75, while the shoulder 141 on the plug body 132 securely abuts against the seat 126 in the hollow 75. The cap 132, which is of greater diameter than the housing 70, presses tightly against the downstream end 76 of the housing 70. When the plug is thus positioned, the face 144 of the reduced diameter section 140 surrounding the protruding extension 142 presses firmly against the second O-ring 96, and the extension 142 itself fills the circular space inside the O-ring 96 and abuts against the downstream face 98 of the cylinder 90, so that the O-ring 96 is tightly wedged axially between the downstream face 99 of the cylinder 90 and the face 144 at the base of the plug body 134, and radially between the protruding extension 142 of the plug body 134 and the walls 79 of the hollow 75.

An elongated rectilinear outlet bore 146 runs axially through the plug 128 from the stem 130 and successively through the cap 132 and the plug body 134 thereof, terminating at the end of the protruding extension 142. When the plug is securely positioned inside the housing 70 of the flow-restriction member 66, as previously described, the outlet bore 146 is in registry with the downstream flow-through passage 98 and forms a fluid path continuation thereof, providing a fluid outlet means for the egress of fluid from the housing 70. A fluid flow path portion is thereby defined by the upstream passage 74, the throat passage bore 88, the downstream passage 98 and the outlet bore 146.

In accordance with the embodiment of the invention illustrated in FIG. 1 and heretofore described, a direct fluid flow path is constituted by the drip chamber 28, the outflow tubing section 32, the four-way tubing joint 36, the connecting tubing section 57, the upstream flow-through passage 74, the throat passage 88, the downstream flow-through passage 98 and the outlet bore 146, all of which are in mutual, successive fluid communication. What has been referred to as the "upstream fluid path portion" comprises, in the embodiment illustrated in the drawings, the outflow tubing section 32, the four-way tubing joint 36, the upstream tubing section 57 and the flow-through passage 74.

The stem 130 of the plug 128 is frictionally connected to the arm 52 of the downstream Y-shaped tubing joint 48. The tubing joint 48 is in turn attached to and in fluid communication by way of its arm 46 with the return tubing section 50 which forms a portion of the bypass flow path in which the variable resistance device 44 is situated. The joint 48 is also connected by way of an arm 145 to a terminal tubing section 147. It may thus be seen that the bypass flow path is in parallel with the portions of the direct flow path situated between the four-way tubing joint 36 and the downstream tubing joint 48.

Because of the pressure and fluid communication provided by the conduit 62 between the four-way tubing joint 36 in the upstream flow path portion and the upstream fluid receiving chamber 58 of the pressure transducer 60, the pressure of the fluid in said upstream chamber 58 is substantially equal to the lateral component of the pressure of the fluid flowing through said tubing joint 36, denoted as $P_1$ in FIG. 1. Similarly, the pressure of fluid in the downstream fluid receiving chamber 122 is equal to the lateral component of the pressure of the fluid flowing out and immediately downstream of the throat passage 88, with which said downstream transducer chamber 122 is in fluid and pressure communication via the radial channels 102, the holes 104, the L-shaped bores 106, the openings 112, the outlet 116, the pressure communicating passage 114, and the lateral tubing section 120. This pressure is denoted $P_2$ in FIG. 1.

When the adjustable clamp 34 shown in FIG. 1 is in any position other than fully closed, fluid will flow from the storage bag 14 through the drip chamber 28 and thence into the direct fluid flow path described above. Fluid reaching the end of the flow-passage 74, which is located at the interface of the extension 77 and the disc 86, is forced by its pressure head to flow through the narrow throat passage defined by the bore 88 in the disc 86. A filtration system (not shown) can be incorporated into the fluid flow path upstream of the tubing joint 36 to ensure that particulate matter, such as dextrose or salt particles, does not clog the throat passage. The fluid emerges from the bore 88 and traverses the bowl-shaped recess 97, entering the portal 100 of the downstream flow-through passage 98.

As is well known to all those skilled in the art of hydraulics or fluid dynamics, Bernoulli's law provides that, with respect to frictionless fluid flowing in a non-turbulent laminar fashion through a tube, the velocity of the flow will be greater where the tube is narrower and, in addition, the pressure of the fluid in the narrowed or constricted area of the tube will be lower than the pressure at points upstream and downstream of the constricted area. In mathematical terms, Bernoulli's law provides that $\frac{1}{2}\rho V^2 + \rho gh$ P is constant, where $\rho$ is the density of the fluid (presumably constant), v is the velocity of the fluid at any given point, g is the gravitional constant, h is the height of the fluid above a particular reference level and P is the pressure of the fluid at the point in question. The relationship expressed in the formula set forth above between velocity and pressure is substantially independent of the viscosity of the fluid in question and thus there is no viscosity term in this formula.

It is a corollary of Bernoulli's law that wherever the velocity of a frictionless constant density fluid is increased, its pressure will decrease, and its velocity is increased when the cross-sectional flow-through area of a tube through which the fluid is flowing decreases. Furthermore, because the velocity term in the Bernoulli's equation is squared, the rate of decrease in pressure of the fluid flowing into the section of reduced cross-sectional area is not constant but accelerates as the velocity of the fluid entering that section increases. Thus, fluid flowing at a higher rate into the constricted area will experience a greater proportionate pressure drop than fluid flowing at a lower rate. All of the above is applicable even to fluids of substantially varying viscosities.

Although in practical applications it is rare that one encounters even approximately frictionless fluids or completely non-turbulent laminar flow, Bernoulli's law is normally applicable at least to the extent that a drop in pressure can be expected when fluid driven by a constant pressure head passes through tubing or pipe sections of reduced cross-sectional area. Moreover, the higher the velocity of the fluid entering the constricted section, the greater will be the drop in pressure observed across the constricted section. It is precisely this principle which enables the operation of the flow-rate sensing device of the present invention.

As fluid begins to flow out of the storage bag 14, through the drip chamber 28 and the outflow tubing section 32, it reaches the four-way tubing joint 36, where a portion of the fluid will flow through the arm 40 of the tubing joint 36 and through the conduit section 62, and thence into the upstream fluid receiving chamber 58 of the transducer 60. The remaining fluid either flows through the arm 38 of the joint 36 into the bypass flow path or continues on the upstream portion of the direct flow path, flowing through the connecting tubing section 57 into the flow restriction member 66.

The fluid which reaches the flow restriction member 66 passes through the upstream passage 74 and is eventually forced through the throat passage formed by the disc 86 and the bore 88. Some fluid emerging from the bore 88 will flow to the periphery of the bowl-shaped recess 97 and thence through the channels 102 and the holes 104 into the L-shaped bores 106, emerging from the openings 112 in the lateral walls of the cylinder 90 and into the annular cavity 95 surrounding those walls. The O-ring 96 prevents the escape of fluid axially downstream from the cavity 95. The fluid in the cavity 95 then passes through the outlet 116 into the pressure communicating passage 114 and proceeds through the lateral stem 118 and the lateral tubing section 120, finally flowing into the dead-end downstream chamber 122 of the pressure transducer 60.

As the rate of the fluid flow through the throat passage increases as a result, for example, of gravitational force (as in the system shown in FIG. 1), the velocity of fluid flow in the throat passage becomes significantly greater than the velocity of the fluid in the upstream fluid path portion, and the pressure of the fluid in the throat passage ($P_2$), as measured in a direction generally normal to the direction of fluid flow, becomes significantly less than the normal component of the pressure in the upstream fluid path portion ($P_1$), in accordance with Bernoulli's law.

A portion of the fluid flowing through the bore 88 flows into the cavity 95 and thence through the pressure communicating passage 114 and the associated conduit elements into the downstream transducer chamber 122. As the velocity of the fluid flowing through the throat passage increases and the normal component of the pressure ($P_2$) in that passage and in the bowl-shaped recess immediately outside that passage accordingly decreases, a marked pressure drop is laterally communicated to the downstream transducer chamber 122, so that the pressure differential between the upstream and downstream transducer chambers will equal the lateral pressure drop experienced by the fluid as it passes through the throat passage, or $P_1-P_2$. This pressure differential between the transducer chambers causes the diaphragm 124 to be substantially deflected by the pressure of the fluid in the upstream chamber 58 towards the downstream chamber 122, because the chamber 58 remains filled with fluid under the same pressure as the fluid in the upstream flow path portion no matter what rate of flow is achieved. As the flow rate is decreased by the flow control mechanism, which will be further described, fluid gradually returns to the downstream transducer chamber 122 and the pressure ($P_2$) in that chamber accordingly increases, causing the diaphragm 124 to move back toward a predetermined equilibrium position. The precise position of the diaphragm at equilibrium is, of course, dependent on the flow rate desired to be achieved or the magnitude of the transducer signal to be outputted.

So long as fluid is flowing through the direct fluid flow path, $P_2$ will be less than $P_1$ because of the drop in pressure caused when the fluid traverses the throat passage. The greater the velocity of the fluid flowing through the flow restriction member 66, the greater the pressure differential between the two chambers of the transducer will be.

The line of action 148 shown in FIG. 1 indicates the transmission of the mechanical signal generated by the movement of the diaphragm 124, which transmission can optionally be made through a second transducer 150, to a signal receiving system. The nature of this signal receiving system depends on the desired function of the flow rate sensing device and the system into which it is incorporated. In the system shown in FIG. 1, for example, the flow rate sensing device is shown functioning as a flow rate regulator and, thus, the system which receives the signal from the pressure transducer 60 directly or through the second transducer 150 is a flow control arrangement, such as a valve system 152 positioned upstream of the tubing joint 36. This valve system can comprise, for example, a solenoid-type valve which is opened to a greater or lesser degree depending on the amount of current passing through the solenoid coil. In that case, the second transducer 150 would be a mechanical-to-electrical transducer, e.g., a standard wiper arm arrangement, which would cause the solenoid valve to gradually close as the rate of flow in the system, and hence the pressure differential between the transducer chambers and the magnitude of the mechanical signal outputted by the transducer 60, increases above a pre-determined level. When the valve 152 is closed to such a degree that the rate of flow through the system falls below a predetermined level, and the pressure differential between the chambers of the transducer 60 and hence the mechanical signal received by the second transducer 150 decreases in magnitude, the valve 152 opens to permit a greater rate of flow through the system.

Of course, the valve system 152 can also include a variety of standard spring or otherwise mechanically actuated valves of dimensions small enough to be used with narrow intravenous tubing, and in that case a direct mechanical connection could exist between the pressure transducer 60 and the valve system 152, or an intervening second transducer 150, consisting of a mechanical-to-mechanical transducing arrangement such as a system of gears, levers and/or springs, could be utilized. Furthermore, the valve system or other flow control means 152 need not be positioned upstream of the flow restriction member 66 but can be effectively positioned intermediate the flow restriction member and the point of administration to the patient.

The flow rate sensing device of the present invention thus can be utilized in conjunction with flow control elements to maintain a constant rate of outflow from a liquid administration system, which is highly desirable in many bio-medical applications, without requiring external means for pressurizing the fluid emerging from the storage container or a complex means for sharply dropping the pressure to create a very large pressure differential on the upstream and downstream sides of a transducer membrane, as in the prior art device U.S. Pat. No. 4,043,332. Instead, the natural pressure drop created by forcing the fluid to pass through a constricted conduit section is utilized to actuate a sensitive auto-feedback control mechanism.

Moreover, the flow rate sensing device described herein and any suitable flow control arrangement incorporating the same are capable of functioning substantially independently, within predetermined limits, of changes in the viscosity or head pressure of the fluid entering the flow restriction member 66, and can precisely sense and/or regulate flow rate notwithstanding changes in mechanical resistance in the system. Hence, the device is most useful in conjunction with intravenous fluid delivery systems, as typefied by FIG. 1, wherein the height differential between the fluid reservoir and the point of entry into the patient's circulation (as well as the viscosity of the fluid selected and the resistance to outflow created by the back pressure of the patient's venous circulation) may all vary.

In the typical intravenous system shown in FIG. 1, the fluid emerging from the outlet bore 146 subsequently flows through the terminal tubing section 147 into a hollow intravenous needle 156, fitted on the end of the tubing section 147, which is adapted for insertion into a vein of a patient. Of course, the system described and shown in FIG. 1 can be adapted for administration of medicinal, nutritive or other therapeutic fluids to a patient by other than intravenous means, for example, intra-cardiac or intra-arterial administration, in which case suitable means for conveying the fluid to the desired location in the patient's body would be utilized in place of the downstream tubing-intravenous needle arrangement shown in FIG. 1.

As is well known to physicians and others engaged in the health professions, the venous blood pressure of a human patient, which can range between, e.g., 5 and 20 millimeters of mercury, or the internal pressure in any other organ or vessel into which the administering needle is inserted, causes a back pressure resisting the flow of fluid from the needle into the patient. In addition, this venous or other pressure fluctuates widely in accordance with the condition of the patient, the positioning of the patient, whether the patient is resting, moving, sleeping, or coughing, and so on. This fluctuating back pressure frequently causes the rate of flow in standard intravenous and other fluid-administration systems to fluctuate widely, as there is no mechanism provided to compensate for increased or decreased resistance to the outflow of fluid from the administering needle. However, in the system shown in FIG. 1, which incorporates the flow rate sensing device of the present invention, the problem of back pressure and fluctuations therein is substantially compensated for and corrected by the flow rate sensing device itself. Any change in the back pressure on the needle 156 which is more than fleeting will be transmitted back to the throat passage, which will effectuate an adjustment in the pressure differential between the upstream chamber 58 and the downstream chamber 122 of the transducer 60, and the flow control arrangement actuated by the transducer 60 will compensate for the increased or decreased back pressure in the line by increasing or decreasing fluid flow accordingly to maintain the desired flow rate. In FIG. 1, $P_3$ represents the back pressure caused in the flow line by venous flow or other conditions.

Adjustment of the sensitivity of the flow rate regulating system illustrated in FIG. 1 can be accomplished by a variety of means, utilized individually or in tandem. For example, the diaphragm 124 can be made adjustable to different tension settings, thus increasing or decreasing the pressure differential (hence the flow rate) necessary to displace the diaphragm sufficiently to activate the flow control arrangement 152. In addition, or alternatively, the optional second transducer 150 can be made adjustable to different signal receiving sensitivities or signal outputting magnitudes. Likewise, the flow control arrangement 152 can be made adjustable to provide varying degrees of flow rate change for any given input signal.

The variable resistance device 44 which is positioned in the bypass flow path in parallel to a portion of the direct fluid flow path is an optional element and is not required in any system incorporating the flow rate sensing device of the present invention. However, the use of a variable resistance device in a parallel flow path greatly increases the range of flow rates which can be accurately provided by a flow regulating system incorporating the subject flow rate sensing device. This increased range of flow rates is provided for the following reasons:

The net driving pressure in a gravity-based system, such as illustrated in FIG. 1, is the difference between the head pressure of the fluid emerging from the reservoir and the back pressure on the needle and terminal tubing section created by the patient's venous pressure and other factors, or $P_0-P_3$, to use the notations of FIG. 1. The head pressure of the fluid is, in turn, a direct function of the height differential between the fluid reservoir and the point of administration to the patient. That height differential is severely restricted by practical considerations and, in the normal hospital setting, would probably not exceed 60–80 centimeters. Thus, there is a natural limitation in a gravity-based system on the maximum flow rate that can be achieved, said limitation being dependent on the maximum allowable height differential, the back pressure at the end of the downstream end of the administration system and the resistance to flow through the system.

In the device illustrated in FIG. 1, there is a tremendous amount of resistance to flow in the direct fluid flow path because fluid is forced to pass through the relatively very narrow throat passage before it can reach the point of administration, and since the net driving pressure cannot be increased beyond a given point for the reasons previously stated, the maximum achievable flow rate would be of a relatively low order if all fluid flowing from the reservoir to the point of administration had to pass through the throat passage in the flow restriction member 66.

By providing a bypass flow path which extends from the fourway tubing joint 36 to the downstream tubing joint 48, a parallel path of greatly reduced resistance in comparison with the direct fluid flow path is created. When the variable resistance device 44 is in fully opened condition so that the tubing sections of the bypass flow path are unconstricted, the resistance to flow in the bypasss flow path will be miniscule in comparison with the resistance through the direct fluid flow path. Thus, a large volume of fluid flow will pass through the bypass flow path (in comparison with flow through the direct flow path), which volume can be closely regulated and adjusted by adjustment of the variable resistance device 44. The total of fluid output (i.e., the aggregate output from the direct and bypass flow paths) is controlled and regulated by the pressure transducer 60 in cooperation with the valve or other flow rate control 152 (which is responsive to increases and decreases in flow rate from the desired level), but the maximum fluid flow rate achievable through the use of a bypass is many times greater than it would be absent such an alternative parallel flow path.

Another method for increasing the range of flow rate control in a system such as that shown in FIG. 1 is to provide multiple flow sensing devices, each including a flow restriction member 66 and a transducer 60, in parallel flow paths, so that each flow restriction member will create only a relatively small pressure drop to be sensed by its associated transducer. The individual pressure transducer signals would then be additively transmitted to an intermediate transducer or to a flow control arrangement directly to cause the desired flow rate adjustment. Alternatively, multiple flow restriction members could be provided in parallel, all in pressure communication with a common pressure transducer. The pressure differential sensed by the transducer would then be the approximate average of the differentials created by each of the flow restriction members, which would be a relatively small differential to be responded to by the transducer diaphragm, and yet high flow volume and flow rate could be achieved.

The flow rate sensing device of the present invention is by no means limited to use in a system for regulating the rate of flow of fluid. The transducer 60 shown in FIG. 1 herein could be connected, either through a second transducer 150 or directly, to a variety of signal receiving systems which would be variably actuated depending on the rate of flow in the fluid system and the resulting magnitude of the signal put out by the transducers. For example, the transducer 60, with or without a second transducer 150, could be connected to an electronic visual display system, either digital, graphic, analog or other, which would indicate to the operator the precise rate of flow through the fluid system at any point in time.

In another application of the device of the present invention, the transducer can be linked to an alarm system to alert hospital or other health care personnel to a potentially dangerous reduction or increase in the rate of flow of the fluid being administered to the patient. Still further, the transducer could be linked to a second flow line carrying another liquid being administered to the patient to regulate the rate of flow of that second liquid in accordance with variations in the rate of flow of the first liquid.

Those skilled in the medical arts and the art of biomedical devices will readily perceive various other useful applications for the flow rate sensing device of the present invention and various ways in which such devices can be incorporated into conventional and state-of-the-art bio-medical systems.

The flow rate sensing device of the present invention, including the flow restriction member, the pressure transducer and the tubing and other conduit elements associated therewith are all preferably made from heat resistant synthetic plastic material, for example, methyl methacrylate, with the exception of the disc 86 and the pressure communicating cylinder 90, which may be fashioned of corrosion-free metal, metal alloy, nylon or synthetic plastic material. The device of the present invention can be fashioned relatively inexpensively so that it can be made disposable when sterilization and further use are no longer feasible, such as when clogging or cracking of any of the components may have occurred. Of course, use of a filtration system, described previously as being an optional component, will help avoid clogging of the throat passage by particulate matter.

All elements of the flow rate sensing device of the present invention which have been described in the preferred embodiment as "tubing sections" are preferably medical grade, resilient, flexible plastic tubing, but may also comprise, where suitable, conduits or tubes of rigid plastic material, glass, metal alloy and so on.

Sterilization of the flow rate sensing device can be easily effected under normal circumstances by unscrewing the plug 128 from the hollow 75 in the housing 70 and removing the O-rings 80 and 96, the disc 86 and the pressure communicating cylinder 90 so that all of these elements, as well as the interior of the housing 70 and the flow-through passages 74, 98 and 146 can be thoroughly cleaned and sterilized.

The flow rate sensing device of the present invention can be manufactured in fully functional form even with very small dimensions. For example, a device wherein the axial length of the flow restriction member housing 70 was on the order of 1¼ inches and the diameter of the housing was approximately ¾ inch was found to be operative for controlling the rate of flow in a standard gravity system for intravenous administration in conjunction with a suitable valve arrangement.

The invention illustrated and described is not intended to be limited to the details shown and is not intended to be limited to use in an intravenous administration system as illustrated in FIG. 1. Various applications, modifications and structural changes may be made of or in the present invention without departing in any way from its spirit.

Without further analysis, the foregoing will so fully reveal the gist of the present invention that others can, by applying current knowledge, readily adapt it for various uses without omitting features that, from the standpoint of prior art, fairly constitute essential characteristics of the generic or specific aspects of this invention. Therefore, such adaptations should and are intended to be comprehended within the meaning and range of equivalence of the following claims.

What is claimed as new and desired to be protected by Letters Patent is set forth in the appended claims:

1. A flow rate sensing device comprising:
   (a) a housing having a fluid inlet means for permitting ingress of a fluid and a fluid outlet means for permitting egress of the fluid;
   (b) means for forming an upstream flow path portion in fluid communication with the fluid inlet means, said upstream flow path portion having a predetermined median flow-through cross-sectional area;
   (c) means for forming a downstream flow-through passage in fluid communication with the upstream flow path portion and the fluid outlet means; and
   (d) flow rate fluctuation detection means comprising:
      (i) means [in the]within said housing for forming a flow-through throat passage comprising flow passage constricting means and means defining an opening and permitting fluid flow across said flow passage constricting means, the flow-through throat passage being intermediate the upstream flow path portion and the downstream flow-through passage and in fluid communication with both said upstream flow path portion and said downstream flow-through passage, thereby defining a direct fluid flow path from the fluid inlet means successively through the upstream flow path portion, the flow-through throat passage, the downstream flow-through passage, and the fluid outlet means, and said flow-through throat passage having a constricting means comprising a median flow-through cross-sectional area which is substantially less than said predetermined median flow-through cross-sectional area so that a decrease in pressure of the fluid flowing along the path is generated within said flow-through throat passage; and
      (ii) pressure transducer means in fluid and pressure communication with said flow-through throat passage and with the upstream flow path portion, respectively, said pressure transducer means being operative to sense a difference between the lateral fluid pressure of the fluid flowing into the upstream flow path portion and the lateral fluid pressure of the fluid flowing out of said flow-through throat passage and to generate a transducer signal which varies as a function of the sensed difference in pressure, the lateral fluid pressure of the fluid flowing out of said flow-through throat passage being measured immediately adjacent to said flow-through throat passage constricting means by pressure communicating means having an axial bore therethrough and providing fluid communication between the upstream flow path portion and the downstream flow-through passage, said pressure communicating means being provided with means for pressure and fluid communication with the pressure transducer means.

2. A flow rate sensing device of claim 1, wherein pressure is measured in a direction normal to the fluid path.

3. A flow rate sensing device of claim 1, wherein said pressure communicating means comprises a member having an upstream surface abutting said flow-through throat passage constricting means.

4. A flow rate sensing device of claim 3, wherein said flow-through throat passage constricting member comprises a disc with an axial bore therethrough.

5. A flow rate sensing device of claim 3, wherein said upstream face has a concave depression formed therein and is provided with means for pressure and fluid communication between said concave depression and the pressure transducer means.

6. A flow rate sensing device of claim 5, wherein said means for pressure communication between the concave depression and the pressure transducer means comprises shallow radial channels at an interface between the upstream face of the pressure communicating means and the flow-through throat passage constricting member, said channels being oriented substantially normally to the fluid flow path and each of said channels having one end directed toward a portal to the downstream flow-through passage and a distal end in fluid communication with the pressure transducer means.

7. A flow rate sensing device of claim 3, wherein the axial bore through the pressure communicating means flares in the downstream direction from an upstream end thereof.

8. A flow rate sensing device of claim 1, wherein said pressure transducer means comprises a transducer with two fluid receiving chambers, said chambers being separated by a resilient, deformable diaphragm which tends to be displaced away from the chamber having higher fluid pressure therein and toward the chamber having lower fluid pressure therein.

9. A flow rate sensing device of claim 1, wherein the pressure transducer means generates a mechanical transducer signal.

10. A flow rate sensing device of claim 1, wherein the pressure transducer means generates an electrical transducer signal.

11. A flow rate regulating system comprising:
   (a) a flow rate sensing device comprising:
      (i) a housing having a fluid inlet means for permitting ingress of a fluid and a fluid outlet means for permitting egress of the fluid:
      (ii) means for forming an upstream flow path portion in fluid communication with the fluid inlet means, said upstream flow path portion having a predetermined median flow-through cross-sectional area;
      (iii) means for forming a downstream flow-through passage in fluid communication with the upstream flow path portion and the fluid outlet means;
      (iv) flow rate fluctuation detection means comprising:
         (A) means within said housing for forming a flow-through throat passage comprising flow passage constricting means and means defining an opening and permitting fluid flow across said flow passage constricting means, the flow-through throat passage being intermediate the upstream flow path portion and the downstream flow-through passage and in fluid communication with both said upstream flow path portion and said downstream flow-through passage, thereby defining a direct fluid flow path from the fluid inlet means successively through the upstream flow path portion, the flow-through throat passage, the downstream flow-through passage, and the fluid outlet means, and said flow-through throat passage having a constricting means comprising a median flow-through cross-sectional area which is substantially less than said predetermined median flow-through cross-sectional area, so that a decrease in pressure of the fluid flowing along the path is generated within said flow-through throat passage; and
         (B) pressure transducer means in fluid and pressure communication with said flow-through throat passage and with the upstream flow path portion, respectively, said pressure transducer means being operative to sense a difference between the lateral fluid pressure of the fluid flowing through said upstream flow path portion and the lateral fluid pressure of the fluid flowing out of said flow-through throat passage and to generate a transducer signal which varies as a function of the sensed difference in pressure, the lateral fluid pressure of the fluid flowing out of said flow-through throat passage being measured immediately adjacent to said flow-through throat passage constricting means by pressure communicating means having an axial bore there through and providing fluid communication between the upstream flow path portion and the downstream flow-through passage, said pressure communicating means being provided with means for pressure and fluid communication with the pressure transducer means; and
   (b) a flow control arrangement operatively connected to the pressure transducer means.

12. A flow rate regulating system of claim 11, wherein pressure is measured in a direction normal to the fluid path.

13. A flow rate regulating system of claim 11, wherein said pressure communicating means comprises a member having an upstream surface abutting said flow-through throat passage constricting means.

14. A flow rate regulating system of claim 11, wherein the flow control arrangement comprises a valve system.

15. A flow rate regulating system of claim 11, wherein there is additionally provided a means for varying the degree of mechanical resistance to fluid flow between a point in the upstream fluid path portion and a point in the direct fluid flow path downstream of the housing.

16. A flow rate regulating system of claim 11 which also comprises variable resistance means in fluid communication with the fluid inlet means and the fluid outlet means.

17. A system for the administration of liquids to a patient, which comprises:
   (a) a liquid reservoir means;
   (b) a conduit means for conveying liquid out of the reservoir means;
   (c) a flow rate regulating system in fluid communication with said conduit means, comprising a flow rate sensing device comprising
      (i) a housing having a fluid inlet means for permitting ingress of a fluid and a fluid outlet means for permitting egress of the fluid;
      (ii) means for forming an upstream flow path portion in fluid communication with the fluid inlet means, said upstream flow path portion having a predetermined flow-through cross-sectional area;
      (iii) means for forming a downstream flow-through passage in fluid communication with the upstream flow path portion and the fluid outlet means;
      (iv) flow rate fluctuation detection means comprising:
         (A) means within said housing for forming a flow-through throat passage comprising flow passage constricting means and means defining an opening and permitting fluid flow across said flow passage constricting means, the flow-through throat passage being intermediate the upstream flow path portion and the downstream flow-through passage and in fluid communication with both said upstream flow path portion and said downstream flow-through passage, thereby defining a direct fluid flow path from the fluid inlet means successively through the upstream flow path portion, the flow-through throat passage, the downstream flowthrough passage, and the fluid outlet means, said flow-through throat passage having a constricting means comprising a median flow-through cross-sectional area which is substantially less than said predetermined median flow-through cross-sectional area, so that a decrease in pressure of the fluid flowing along the path is generated within said flow-through throat passage; and (B) pressure transducer means in fluid and pressure communication with said flow-through throat passage and with the upstream flow path portion, respectively, said pressure transducer means being operative to sense a difference between the lateral fluid pressure of the fluid flowing into the upstream flow path portion and the lateral fluid pressure of the fluid flowing out of said flow-through throat passage and to generate a transducer signal which varies as a function of the sensed difference in pressure, the lateral fluid pressure of fluid flow-through throat passage being measured immediately adjacent to said flow-through throat passage constricting means by pressure communicating means having an axial bore therethrough and providing fluid communication between the upstream flow path portion and the downstream flow-through passage, said pressure communicating means being provided with means for pressure and fluid communication with the pressure transducer means;

(d) a flow control arrangement operatively connected to the pressure transducer means; and (e) means for conveying the liquid from the flow rate regulating system to a desired location in the patient's body.

18. A liquid administration system of claim 17, wherein pressure is measured in a direction normal to the fluid path.

19. A liquid administration system of claim 17, wherein said pressure communicating means comprises a member having an upstream surface abutting said flow-through throat passage constricting means.

20. A liquid administration system of claim 17, wherein the means for conveying the liquid from the flow rate regulating system to the desired location in the patient's body comprises a flexible tubing section having one end in fluid communication with the flow rate regulating system and a second end adjoined to a hollow needle.

21. A liquid administration system of claim 17, which also comprises variable resistance means in fluid communication with the fluid inlet means and the fluid outlet means.

* * * * *

UNITED STATES PATENT AND TRADEMARK OFFICE
CERTIFICATE OF CORRECTION

PATENT NO. : 4,613,325
DATED : September 23, 1986
INVENTOR(S) : LAWRENCE M. ABRAMS It is certified that error appears in the above-identified patent and that said Letters Patent is hereby corrected as shown below:

Col. 6, line 36, delete "to", first occurence.

Col. 17, Claim 1, line 13 thereof, "[in the]within" should read
-- within --.

Col. 20, line 5, "there through" should read -- therethrough --.

Col. 21 line 22, "fluid (second occurrence) should read
-- the fluid flowing out of said --.

Signed and Sealed this

Third Day of March, 1987

Attest:

DONALD J. QUIGG

*Attesting Officer*  *Commissioner of Patents and Trademarks*